US007087213B2

(12) United States Patent
Prusiner et al.

(10) Patent No.: US 7,087,213 B2
(45) Date of Patent: *Aug. 8, 2006

(54) METHOD OF PREPARING COW BRAIN HOMOGENATE

(75) Inventors: Stanley B. Prusiner, San Francisco, CA (US); Jiri G. Safar, Walnut Creek, CA (US)

(73) Assignee: The Regents of the University of California, Oakland, CA (US)

( * ) Notice: Subject to any disclaimer, the term of this patent is extended or adjusted under 35 U.S.C. 154(b) by 42 days.

This patent is subject to a terminal disclaimer.

(21) Appl. No.: 11/054,585

(22) Filed: Feb. 8, 2005

(65) Prior Publication Data

US 2005/0287598 A1  Dec. 29, 2005

Related U.S. Application Data

(63) Continuation of application No. 10/742,241, filed on Dec. 18, 2003, now Pat. No. 6,875,577, which is a continuation of application No. 10/047,431, filed on Jan. 14, 2002, now Pat. No. 6,677,125, which is a continuation of application No. 09/754,443, filed on Jan. 3, 2001, now Pat. No. 6,406,864, which is a continuation of application No. 09/169,574, filed on Oct. 9, 1998, now Pat. No. 6,214,565, and a continuation-in-part of application No. 09/026,967, filed on Feb. 20, 1998, now Pat. No. 5,977,324.

(51) Int. Cl.
A61K 49/00 (2006.01)
A61K 39/42 (2006.01)
G01N 33/53 (2006.01)
C12P 21/04 (2006.01)

(52) U.S. Cl. ............ 424/9.1; 424/147.1; 435/7.1; 435/70.1; 435/71.1; 436/503; 436/518; 436/547; 530/387.1

(58) Field of Classification Search ......... 424/9.1, 424/147.1; 435/7.1, 70.1, 71.1; 436/503, 436/518, 547; 530/387.1
See application file for complete search history.

(56) References Cited

U.S. PATENT DOCUMENTS

| 4,806,627 | A | | 2/1989 | Wisniewski et al. |
| 5,565,186 | A | | 10/1996 | Prusiner et al. |
| 6,214,565 | B1 | * | 4/2001 | Prusiner et al. ............ 435/7.1 |
| 6,406,864 | B1 | * | 6/2002 | Prusiner et al. ............ 435/7.1 |
| 6,677,125 | B1 | * | 1/2004 | Prusiner et al. ............ 435/7.1 |

FOREIGN PATENT DOCUMENTS

| WO | WO 93/10227 | 5/1993 |
| WO | WO 97/43649 | 11/1997 |
| WO | WO 98/37210 | 8/1998 |
| WO | WO 99/42487 | 8/1999 |

OTHER PUBLICATIONS

Anderson et al., (1996) ATransmission dynamics and epidemiology of BSE in British cattle,@ Nature 382: 779-88.
Barry, R.A., et al., (1986) "Monoclonal Antibodies to the Cellular and Scrapie Prion Proteins," Journal of Infectious Diseases 154:518-521.
Basler et al., (1986) "Scrapie and Cellular PrP Isoforms Are Encoded by the Same Chromosomal Gene," Cell 46: 417-28.
Bendheim, et al., (1984) "Antibodies to a Scrapie Prion Protein," Nature 310:418-421.
Bode et al., (1985) "Characterization of Antisera Against Scrapie-Associated Fibrils (SAF) from Affected Hamster and Cross-Reactivity with SAF from Scrapie-Affected Mice and from Patients with Creutzfeldt-Jacob Disease," J. Gen. Virol. 66:2471-2478.
Bolton et al., (1982) "Identification of a Protein That Purifies with the Scrapie Prion," Science 218: 1309-11.
Brown et al., (1992) "'Friendly Fire' in Medicine: Hormones, Homografts, and Creutzfeldt-Jakob Disease," Lancet 340: 24-27.
Buchanan et al., (1991) "Mortality, Neoplasia, and Creutzfeldt-Jakob Disease in Patients Treated with Human Pituitary Growth Hormone in the United Kingdom", BMJ 302:824-828.
Bueler et al., (1992) "Normal Development and Behavior of Mice Lacking the Neuronal Cell-surface PrP Protein," Nature 356:577-582.
Carter, et al., (1992) AHigh Level Escherichia coli Expression and Production of a Bivalent Humanized Antibody Fragment,@ Biotechnology 10:163-7.
Cochius et al., (1992) "Creutzfeldt-Jakob Disease in a Recipient of Human Pituitary-Derived Gonadotrophin: A Second Case," J. Neurol. Neurosurg. Psychiatry 55:1094-1095.
Cochius et al., (1990) "Creutzfeldt-Jakob Disease in a Recipient of Human Pituitary-Derived Gonadotrophin," Aust. N.Z. J. Med. 20:592-593.
Collinge, et al., (1996) APrion protein gene analysis in new variant cases of Creutzfeldt-Jakob disease,@ Lancet 348:56.
Gajdusek, D.C., (1977) "Unconventional Viruses and the Origin and Disappearance of Kuru," Science 197:943-960.
Gibbs, Jr. et al., (1993) "Creutzfeldt-Jakob Disease Infectivity of Growth Hormone Derived from Human Pituitary Glands," N. Engl. J. Med. 328:358-359.

(Continued)

Primary Examiner—Rodney P Swartz
(74) Attorney, Agent, or Firm—Karl Bozicevic; Bozicevic, Field & Francis LLP

(57) ABSTRACT

A method of isolating and detecting the presence of a disease related conformation of a protein (e.g., PrP$^{Sc}$) is disclosed. The sample is treated such as by contacting it with a protease and then contacting the treated sample with a binding partner which binds the PrP$^{Sc}$ which can be isolated and separated from the sample.

13 Claims, No Drawings

OTHER PUBLICATIONS

Goldfarb et al., (1992) "Fatal *Familial insomnia* and Familial Creutzfeldt-Jakob Disease: Disease Phenotype Determined by a DNA Polymorphism," *Science* 258:806-808.

Goldman, W. "PrP gene and its association with spongiform encephalopathies," *British Medical Bulletin* (Oct. 1993) 49(4) :839-59 (Abstract).

Healy et al., "Creutzfeldt-Jakob Disease After Pituitary Gonadotrophins: The Prion is the Problem," *BMJ* (1993) 307:517-518.

Hsiao et al., (1994) ASerial transmission in rodents of neurodegeneration from transgenic mice expressing mutant rion protein,@ *Proc. National Acad. Sci. USA* 91:9126-30.

Kascsak, R.J., et al., (1987) "Mouse Polyclonal and Monoclonal Antibody to Scrapie-Associated Fibril Proteins," *Journal of Virology* 61:3688-3693.

Lasmezas et al., (1993) "Recombinant Human Growth Hormone and Insulin-Like Growth Factor I Induce PRP Gene Expression in PC12 Cell," *Biochem. Biophys. Res. Commun.* 196:1163-1169.

McKinley et al., (1983) "A Protease-Resistant Protein is a Structural Component of the Scrapie Prion," *Cell* 35:57-62.

Mehlhorn et al., (1996) AHigh-Level Expression and Characterization of a Purified 142-Residue Polypeptide of the Prion Protein,@ *Biochemistry* 35:5528-37.

Meyer et al., (1986) "Separation and Properties of Cellular and Scrapie Prion Proteins," *Proc. Natl. Acad. Sci. USA* 83: 2310-2314.

Oesch, et al., (1985) "A Cellular Gene Encodes Scrapie PrP 27-30 Protein," *Cell* 40: 735-46.

Pan, et al., (1993) AConversion of α-helics into β-sheets features in the formation of the scrapie prion proteins,@ *Proc. Natl. Acad. Sci. USA* 90:10962-66.

Pan, et al., (1992) "Purification and Properties of the Cellular Prion Protein from Syrian Hamster Brain," *Protein Sci.* 1:1343-1352.

Prusiner, S.B., et al., (1983) "Scrapie prions aggregate to form amyloid-like birefringent rods," *Cell* 35: 349-58.

Prusiner, S.B. et al., ABiology of Prions,@ *The Molecular and Genetic Basis of Neurological Disease*, 2nd Edition, Chap. 7, pp. 103-143.

Rogers et al., (1991) "Epitope Mapping of the Syrian Hamster Prion Protein Utilizing Chimeric and Mutant Genes in a Vaccinia Virus Expresion System," *J. Immunol.* 147: 3568-74.

Rogers, et al., (1993) AConversion of truncated and elongated prion proteins into the scrapie isoform in cultured cells,@ *Proc. Natl. Acad. Sci. USA* 90:3182-6.

Safar et al. J., (1993) AConformational Transitions, Dissociation, and Unfolding of Scrapie Amyloid (Prion) Protein,@ *J. Biol. Chem.* 268: 20276-84.

Safar, et al., (1990) AScrapie-associated precursor proteins: Antigenic relationship between species and immunocytochemical localization in normal, scrapie, and Creutzfeldt-Jakob disease brains,@ *Neurology* 40: 513-7.

Schmerr, Mary Jo et al., (1996) "Improvements in a Competition Assay to Detect Scrapie Prion Protein by Capillary Eletrophoresis", *Journal of Chromatography B* 681:29-35.

Serban et al, (1990) "Rapid Detection of Creuzfeldt-Jakob Disease and Scrapie Prion Proteins," *Neurology* 40:110-7.

Stahl et al., (1993) AStructural Studies of the Scrapie Prion Protein Using Mass Spectrometry and Amino Acid Sequencing,@ *Biochemistry* 32: 1991-2002.

Taraboulos et al., (1992) "Regional Mapping of Prion Proteins in Brain," *Proc. Natl. Acad. Sci. USA* 89:7620-7624.

Turk, et al., (1988) "Purification and Properties of the Cellular and Scrapie Hamster Prion Proteins," *Eur. J. Biochem.* 176:21-30.

Wilesmith and Wells, (1991) ABovine Spongiform Encephalopathy,@ *Curr. Topics Microbiol. Immunol.* 172 21-38.

Wilesmith, ABovine Spongiform Encephalopathy,169 *Methods in Molecular Medicines: Prion Diseases*, pp. 155-73.

Williamson, et al., (1996) ACircumventing tolerance to generate autologous monoclonal antibodies to the prion protein,@ *Proc. Natl. Acad. Sci. USA* 93: 7279-82.

Yokoyama, Takashi, et al., (1996) "Immunoreactivity of Specific Epitopes of PrP$^{sc}$ is Enhanced by Pretreatment in a Hydrated Autoclave", *Clinical and Diagnostic Laboratory Immunology* 3(4):470-471.

\* cited by examiner

METHOD OF PREPARING COW BRAIN HOMOGENATE

CROSS-REFERENCES

This application is a continuation of U.S. application Ser. No. 10/742,241 filed Dec. 18, 2003, now issued U.S. Pat. No. 6,875,577 on Apr. 5, 2005, which is a continuation of U.S. application Ser. No. 10/047,431, filed Jan. 14, 2002, now issued U.S. Pat. No. 6,677,125 on Jan. 13, 2004, which is a continuation application of Ser. No. 09/754,443, filed Jan. 3, 2001, now issued U.S. Pat. No. 6,406,864 on Jun. 18, 2004 which is a continuation application of U.S. application Ser. No. 09/169,574, filed Oct. 9, 1998, now issued U.S. Pat. No. 6,214,565 on Apr. 10, 2001, and further is a continuation-in-part of U.S. application Ser. No. 09/026,967, filed Feb. 20, 1998, issued as U.S. Pat. No. 5,977,324 on Nov. 2, 1999, all of which are incorporated herein by reference in their entirety and to which applications is claimed priority under 35 U.S.C. §120.

GOVERNMENT RIGHTS

The United States Government may have certain rights in this application pursuant to Grant No. AG02132, AG10770, NS22786, NS14069, and NS07219 awarded by the National Institutes of Health.

FIELD OF THE INVENTION

This invention relates to the field of bioassays and more particularly to an assay which makes it possible to isolate and detect a disease conformation of a protein present in a native sample also containing a non-disease conformation of the protein.

BACKGROUND OF THE INVENTION

Prions are infectious pathogens that cause invariably fatal prion diseases (spongiform encephalopathies) of the central nervous system in humans and animals. Prions differ significantly from bacteria, viruses and viroids. The dominating hypothesis is that no nucleic acid is necessary to allow for the infectivity of a prion protein to proceed.

A major step in the study of prions and the diseases they cause was the discovery and purification of a protein designated prion protein [Bolton, McKinley et al. (1982) *Science* 218:1309–1311; Prusiner, Bolton et al. (1982) *Biochemistry* 21:6942–6950; McKinley, Bolton et al. (1983) *Cell* 35:57–62]. Complete prion protein-encoding genes have since been cloned, sequenced and expressed in transgenic animals. $PrP^C$ is encoded by a single-copy host gene [Basler, Oesch et al. (1986) *Cell* 46:417–428] and when $PrP^C$ is expressed it is generally found on the outer surface of neurons. Many lines of evidence indicate that prion diseases results from the transformation of the normal form of prion protein ($PrP^C$) into the abnormal form ($PrP^{Sc}$). There is no detectable difference in the amino acid sequence of the two forms. However, $PrP^{Sc}$ when compared with $PrP^C$ has a conformation with higher β-sheet and lower α-helix content [Pan, Baldwin et al. (1993) *Proc Natl Acad Sci USA* 90:10962–10966; Safar, Roller et al. (1993) *J Biol Chem* 268:20276–20284]. The presence of the abnormal $PrP^{Sc}$ form in the brains of infected humans or animals is the only disease-specific diagnostic marker of prion diseases.

$PrP^{Sc}$ plays a key role in both transmission and pathogenesis of prion diseases (spongiform encephalopathies) and it is a critical factor in neuronal degeneration [Prusiner (1997) The Molecular and Genetic Basis of Neurological Disease, 2nd Edition: 103–143]. The most common prion diseases in animals are scrapie of sheep and goats and bovine spongiform encephalopathy (BSE) of cattle [Wilesmith and Wells (1991) *Curr Top Microbiol Immunol* 172:21–38]. Four prion diseases of humans have been identified: (1) kuru, (2) Creutzfeldt-Jakob Disease (CJD), (3) Gerstmann-Streussler-Sheinker Disease (GSS), and (4) fatal familial insomnia (FFI) [Gajdusek (1977) *Science* 197:943–960; Medori, Tritschler et al. (1992) *N Engl J Med* 326:444–449]. Initially, the presentation of the inherited human prion diseases posed a conundrum which has since been explained by the cellular genetic origin of PrP.

Prions exist in multiple isolates (strains) with distinct biological characteristics when these different strains infect in genetically identical hosts [Prusiner (1997) The Molecular and Genetic Basis of Neurological Disease, 2nd Edition: 165–186]. The strains differ by incubation time, by topology of accumulation of $PrP^{Sc}$ protein, and in some cases also by distribution and characteristics of brain pathology [DeArmond and Prusiner (1997) Greenfield's Neuropathology, 6th Edition: 235–280]. Because $PrP^{Sc}$ is the major, and very probably the only component of prions, the existence of prion strains has posed a conundrum as to how biological information can be enciphered in a molecule other than one comprised of nucleic acids. The partial proteolytic treatment of brain homogenates containing some prion isolates has been found to generate peptides with slightly different electrophoretic mobilities [Bessen and Marsh (1992) J Virol 66:2096–2101; Bessen and Marsh (1992) J Gen Virol 73:329–334; Telling, Parchi et al. (1996) Science 274: 2079–2082]. These findings suggested different proteolytic cleavage sites due to the different conformation of $PrP^{Sc}$ molecules in different strains of prions. Alternatively, the observed differences could be explained by formation of different complexes with other molecules, forming distinct cleavage sites in $PrP^{Sc}$ in different strains [Marsh and Bessen (1994) Phil Trans R Soc Lond B 343:413–414]. Some researchers have proposed that different prion isolates may differ in the glycosylation patterns of prion protein [Collinge, Sidle et al. (1996) Nature 383:685–690; Hill, Zeidler et al. (1997) Lancet 349:99–100]. However, the reliability of both glycosylation and peptide mapping patterns in diagnostics of multiple prion strains is currently still debated [Collings, Hill et al. (1997) Nature 386:564; Somerville, Chong et al. (1997) Nature 386:564].

A system for detecting $PrP^{Sc}$ by enhancing immunoreactivity after denaturation is provided in Serban, et al., Neurology, Vol. 40, No. 1, Ja 1990. Sufficiently sensitive and specific direct assay for infectious $PrP^{Sc}$ in biological samples could potentially abolish the need for animal inoculations completely. Unfortunately, such does not appear to be possible with current $PrP^{Sc}$ assays—it is estimated that the current sensitivity limit of proteinase-K and Western blot-based $PrP^{Sc}$ detection is in a range of 1 µg/ml which corresponds to $10^4$–$10^5$ prion infectious units. Additionally, the specificity of the traditional proteinase-K-based assays for $PrP^{Sc}$ is in question in light of recent findings of only relative or no proteinase-K resistance of undoubtedly infectious prion preparations [Hsiao, Groth et al. (1994) *Proc Natl Acad Sci USA* 91:9126–9130] Telling, et al. (1996) *Genes & Dev.*

Human transthyretin (TTR) is a normal plasma protein composed of four identical, predominantly β-sheet structured units, and serves as a transporter of hormone thyroxine. Abnormal self assembly of TTR into amyloid fibrils causes two forms of human diseases, namely senile systemic amyloidosis (SSA) and familial amyloid polyneuropathy (FAP) [Kelly (1996) *Curr Opin Strut Biol* 6(1):11–7]. The cause of amyloid formation in FAP are point mutations in the TTR gene; the cause of SSA is unknown. The clinical diagnosis is established histologically by detecting deposits of amyloid in situ in biopsy material.

To date, little is known about the mechanism of TTR conversion into amyloid in vivo. However, several laboratories have demonstrated that amyloid conversion may be simulated in vitro by partial denaturation of normal human TTR [McCutchen, Colon et al. (1993) *Biochemistry* 32(45): 12119–27; McCutchen and Kelly (1993) *Biochem Biophys Res Commun* 197(2) 415–21]. The mechanism of conformational transition involves monomeric conformational intermediate which polymerizes into linear β-sheet structured amyloid fibrils [Lai, Colon et al. (1996) *Biochemistry* 35(20):6470–82]. The process can be mitigated by binding with stabilizing molecules such as thyroxine or triiodophenol [Miroy, Lai et al. (1996) *Proc Natl Acad Sci USA* 93(26):15051–6].

In view of the above points, there is clearly a need for a specific, high flow-through, and cost-effective assay for testing sample materials for the presence of a pathogenic protein including transthyretin and prion protein.

SUMMARY OF THE INVENTION

The assay of the invention involves treating a sample suspected of containing a protein in at least two conformations, i.e., in both a disease conformation and a non-disease conformation. The sample is treated with a compound which hydrolyzes the non-disease related conformation of the protein but neither hydrolyzes or denatures the disease conformation of the protein. After treatment the assay can proceed in two possible ways. In a first method the sample is brought into contact with a binding agent such as an antibody which binds to the disease conformation of the protein so that any detected binding indicates the presence of protein in the disease conformation being present in the sample. In a second method the treated sample is then subjected to a second treatment step which at least partially denatures the disease conformation of the protein so that the denatured protein will bind to a wider range of binding partners. After denaturation the sample is brought into contact with a binding partner which binds the denatured, diseased conformation of the protein.

Depending on the steps used in the assay of the invention one of two types of antibodies may be used. Accordingly, both basic types of assays the sample is treated with a compound, e.g. a metalloendopeptidase, which selectively hydrolyzes $PrP^C$ but not $PrP^{Sc}$. Thereafter, the treated sample can be subjected to two different types of processing, each of which uses a generally different type of antibody.

The first general type of antibody selectively binds to the disease conformation of the protein. For example, antibodies that selectively recognize $PrP^{Sc}$ bind to an epitope on the C-terminus of the protein. When a PrP protein is in its $PrP^{Sc}$ configuration its C-terminus can be bound by antibodies of the type described in WO 97/10505 published Mar. 20, 1997—reference is also made to WO 98/37210 which claims to disclose antibodies which bind $PrP^{Sc}$. Both of these PCT publications are incorporated herein by reference to describe and disclose antibodies and method of making antibodies.

The second general type of antibody binds to both the disease and the non-disease conformations of the protein. For example, antibodies that recognize an epitope on the N-terminus of the PrP protein recognize both $PrP^{Sc}$ and $PrP^C$ following denaturation of the proteins. When the PrP protein is in the $PrP^{Sc}$ configuration the N-terminus is not exposed and as such can not be bound by an antibody. To expose an epitope of the N-terminus the $PrP^{Sc}$ is denatured, e.g. by exposure to guanadine HCl under conditions (pH, temperature, and time) which causes the $PrP^{Sc}$ to unfold or change its 3-dimensional structure such that a C-terminal epitope is exposed. In this unfolded configuration a wide range of binding partner including commercially available antibodies can be used for detection. Since such antibodies also bind $PrP^C$ all of the $PrP^C$ must be removed, e.g., by selective hydrolysis.

An example of an antibody which binds an epitope of the N-terminus is the monoclonal antibody 3F4 produced by the hybridoma cell line ATCC HB9222 deposited on Oct. 8, 1986 in the American Type Culture Collection, 10801 University Boulevard, Manassas, Va. 20110-2209 and disclosed and described in U.S. Pat. No. 4,806,627 issued Feb. 21, 1989—incorporated by reference to disclose antibodies which selectively bind $PrP^C$. In addition to antibody other binding partners which bind the non-disease related conformation but not the disease related conformation could be used in the assay of the invention. Antibodies such as 3F4 and others used in the assays described in the examples are commercially available.

In one embodiment of the invention, one portion of a sample containing two conformations of a protein (e.g. $PrP^C$ and $PrP^{Sc}$) is reacted with a binding partner (e.g. R1) that binds both conformations, and another portion of the same sample is reacted with a binding partner (e.g. 3F4) that binds only one of the two forms (e.g. $PrP^C$). The disease related conformation is determined by comparing the two. If the binding partner which binds both conformations shows more binding than the binding partner which binds only one conformation, this shows that both conformations are present in the sample. For example, if R1 binds to more protein than 3F4, $PrP^{Sc}$ is present in the sample. No hydrolysis treatment is needed with this method. However, pretreatment may be used and comparison of the binding may be adjusted for a variety of factors, e.g. binding affinities, comparisons to known samples, hybridization times, variations in signal due to secondary antibodies, etc.

An aspect of the invention is to provide an immunoassay which is applicable to assaying samples containing proteins, which samples are suspected of containing a protein which occurs within a native non-disease conformation and a disease related conformation (e.g., PrP protein, βA4 protein and transthyretin).

Another aspect of the invention is to provide an assay which differentiates between (1) disease related proteins or portions thereof which are not hydrolyzed by limited protease treatment with a protease such as proteinase K (protease resistant proteins, e.g. PrP 27–30) and (2) disease related proteins which are hydrolyzed by a limited protease treatment with a protease such as proteinase K (e.g., protease-sensitive $PrP^{Sc}$).

An advantage of the present invention is that the immunoassay can quickly and accurately determine the presence of proteins in the disease related conformation (e.g., $PrP^{Sc}$, βA4 and transthyretin) even though the antibody used in the assay does not bind or has a very low degree of binding affinity for the protein in the disease related conformation and the disease related conformation is present in a lower concentration than the non-disease conformation.

A feature of the invention is that the signal obtained can be enhanced by the use of transgenic animals, e.g., mice which are used to detect the presence of a protein in a sample.

Another feature is that time-resolved, dissociation-enhanced fluorescence or a dual wavelength, laser driven fluorometer can be used to enhance sensitivity.

Another advantage is that the assay can detect levels of the disease causing conformation of a protein at a concentration of $1 \times 10^3$ particles/ml or less.

A specific object is to provide a diagnostic assay for determining the presence of infectious prion protein in variable sample materials obtained or derived from human, primate, monkey, pig, bovine, sheep, goat, deer, elk, cat, dog, mouse, chicken, and turkey tissues and/or body fluids.

Another specific object is to provide a diagnostic assay for determining the presence of βA4 protein in variable sample materials obtained or derived from human, primate, monkey, pig, bovine, sheep, goat, deer, elk, cat, dog, mouse, chicken, and turkey tissues and/or body fluids.

Another object is to provide a rapid assay for native infectious prion protein in the brains of transgenic and non-transgenic animals injected with sample material potentially containing prions.

Another object is to provide a method to evaluate decontamination procedures by assaying the level of denaturation of pathogenic proteins (e.g., prions or β-sheet βA4) after such treatments.

Another advantage is that the process can be carried out without an antibody directly able to recognize an infectious conformation of a protein, and without using a proteinase K step to eliminate the signal of normal (non-disease) isoforms of the protein such as $PrP^c$.

Another advantage is that in the invented process there is no need for the antibody directly able to recognize a pathogenic conformation of βA4 or transthyretin.

An important feature of the assay is the rapid, cost effective and high flow-through design which can be designed with the capacity to screen 96 samples per day per 96 well plate.

Another aspect of the invention is the diagnostic method to quantitatively detect TTR in the abnormal, amyloid conformation in sample material obtained from human and animal tissues, body fluids, and pharmaceuticals.

The invented process provides a direct, sensitive method to distinguish and quantify the normal and amyloid conformations of TTR in a mixture present in sample materials.

An important object is to provide specific diagnostic assay for pathogenic TTR in variable sample materials obtained or derived from human, primate, monkey, pig, bovine, sheep, deer, elk, cat, dog, and chicken tissues.

Another object is to provide a rapid assay for amyloid form of TTR in transgenic animals.

The specific advantage is that invented assay may detect pathogenic forms of TTR in a mixture with denatured nonpathogenic forms of the same or in a mixture with a soluble form of TTR—for example, detect less than $1 \times 10^3$ particles per ml.

These and other objects, advantages, and features of the invented process will become apparent to those skilled in the art upon reading the details of the assay method, antibody development and testing, and transgenic mouse as more fully described below with reference to the attached figures.

DETAILED DESCRIPTION OF THE PREFERRED EMBODIMENTS

Before the present assays and methods are disclosed and described, it is to be understood that this invention is not limited to particular antibodies, proteins, labels, assays or methods as such may, of course vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for the disclosure prior to the filing date of the present application. Nothing herein is to be construed as an admission that the present invention is not entitled to antedate such publication by virtue of prior invention. Further, the dates of the publications provided are subject to change if it is found that the actual date of publication is different from that provided here.

Definitions

The term "protein" as used herein is intended to encompass any amino acid sequence and include modified sequences such as glycoproteins. The term includes naturally occurring proteins and peptides as well as those which are recombinantly or synthetically synthesized. As used in connection with the present invention the term "protein" is specifically intended to cover naturally occurring proteins which occur in at least two different conformations wherein both conformations have the same or substantially the same amino acid sequence but have different three dimensional structures. The two conformations of the protein include at least one conformation which is not related to a disease state and at least one conformation which is related to a disease state—pathogenic. A specific and preferred example of a protein as used in connection with this disclosure is a PrP protein which includes the non-disease form referred to as the $PrP^c$ form and the disease related form referred as the $PrP^{Sc}$. Although a prion protein or the $PrP^{Sc}$ form of a PrP protein is infectious and pathogenic, the disease conformation of other proteins is not infectious although it is pathogenic. As used herein, the term pathogenic may mean that the protein actually causes the disease or it may simply mean that the protein is associated with the disease and therefore is present when the disease is present. Thus, a pathogenic protein as used in connection with this disclosure is not necessarily a protein which is the specific causative agent of a disease.

The terms "pretreatment", "unfolding treatment", and "limited protease treatment" are intended to encompass the descriptions and use of these terms as provided in the respective sections having these headings.

The terms "PrP protein", "PrP" and like are used interchangeably herein and shall mean both the infectious particle form $PrP^{Sc}$ known to cause diseases (spongiform encephalopathies) in humans and animals and the noninfectious form PrP$^C$ which, under appropriate conditions is converted to the infectious PrP$^{Sc}$ form.

The terms "prion", "prion protein" and "PrP$^{Sc}$ protein" and the like we used interchangeably herein to refer to the infectious PrP$^{Sc}$ form of PrP, and is a contraction of the words "protein" and "infection." Particles are comprised largely, if not exclusively, of PrP$^{Sc}$ molecules encoded by a PrP gene. Prions are distinct from bacteria, viruses and viroids. Known prions infect animals to cause scrapie, a transmissible, degenerative disease of the nervous system of sheep and goats, as well as bovine spongiform encephalopathy (BSE), or "mad cow disease", and feline spongiform encephalopathy of cats. Four prion diseases known to affect humans are (1) kuru, (2) Creutzfeldt-Jakob Disease (CJD), (3) Gerstmann-Straussler-Scheinker Disease (GSS), and (4) fatal familial insomnia (FFI). As used herein "prion" includes all forms of prions causing all or any of these diseases or others in any animals used—and in particular in humans and domesticated farm animals.

The term "PrP gene" is used herein to describe genetic material which expresses proteins including known polymorphisms and pathogenic mutations. The term "PrP gene" refers generally to any gene of any species which encodes any form of a PrP protein. Some commonly known PrP sequences are described in Gabriel et al., *Proc. Natl. Acad. Sci. USA* 89:9097–9101 (1992), and U.S. Pat. Nos. 5,565,186; 5,763,740; 5,792,901; and WO97/04814, incorporated herein by reference to disclose and describe such sequences. The PrP gene can be from any animal, including the "host" and "test" animals described herein and any and all polymorphisms and mutations thereof, it being recognized that the terms include other such PrP genes that are yet to be discovered. The protein expressed by such a gene can assume either a PrP$^C$ (non-disease) or PrP$^{Sc}$ (disease) form.

The term "binding partner" refers to any molecule which binds the target molecule of interest. Preferably, the binding is of sufficiently high affinity as to make it possible to bind target molecules of interest present in a low concentration, e.g., 1×10$^3$ particles per ml or less. More preferably the binding partner is selective in binding only the target molecule and not other molecules. Preferred binding partners are antibodies as defined below.

The term "antibody" stands for an immunoglobulin protein which is capable of binding an antigen. Antibody as used herein is meant to include the entire antibody as well as any antibody fragments (e.g. F(ab)', Fab, Fv) capable of binding the epitope, antigen or antigenic fragment of interest. Antibodies for assays of the invention may be immunoreactive or immunospecific for and therefore specifically and selectively bind to a protein of interest e.g., an A4β amyloid protein or a PrP protein. Antibodies which are immunoreactive and immunospecific for both the native non-disease form and the treated disease form but not for the untreated disease form, (e.g., for both native PrP$^C$ and treated PrP$^{Sc}$ but not native PrP$^{Sc}$) may be used because the sample is treated to remove i.e., hydrolyze PrP$^C$. Antibodies for PrP are preferably immunospecific—e.g., not substantially cross-reactive with related materials. Some specific antibodies which can be used in connection with the invention are disclosed in published PCT application WO 97/10505 which is incorporated herein by reference to disclose and describe antibodies. This published PCT application corresponds to U.S. Ser. No. 08/713,939. Antibodies disclosed in the PCT application which bind PrP$^{Sc}$ can be used to carry out the basic assay of the present invention when the sample has been treated with dispase sufficiently to hydrolyze all or substantially all of the PrP$^C$ present in the sample. Another useful antibody for binding to PrP$^C$ is the monoclonal antibody 263K 3F4 produced by the hybridoma cell line ATCC HB9222 deposited on Oct. 8, 1986 in the American Type Culture Collection, 10801 University Boulevard, Manassas, Va. 20110-2209 and disclosed and described in U.S. Pat. No. 4,806,627 issued Feb. 21, 1989—incorporated by reference to disclose antibodies which selectively bind PrP$^c$. The term "antibody" encompasses all types of antibodies, e.g. polyclonal, monoclonal, and those produced by the phage display methodology. Particularly preferred antibodies of the invention are antibodies which have a relatively high degree of affinity for both native PrP$^C$ and treated PrP$^{Sc}$ but a relatively low degree of or substantially no binding affinity for PrP$^{Sc}$. More specifically, antibodies of the invention preferably have four times or more, more preferably fifteen times or more, and still more preferably 30 times or more binding affinity for both native PrP$^C$ and denatured PrP$^{Sc}$ as compared with the binding affinity for native PrP$^{Sc}$.

"Purified antibody" refers to that which is sufficiently free of other proteins, carbohydrates, and lipids with which it is naturally associated. Such an antibody "preferentially binds" to a denatured disease conformation of a protein such as the denatured β-sheet conformation of A4β or PrP$^{Sc}$ protein (or an antigenic fragment thereof), and does not substantially recognize or bind to other antigenically unrelated molecules. A purified antibody of the invention is preferably immunoreactive with and immunospecific for a specific species and more preferably immunospecific for native PrP$^C$ and for denatured forms of PrP$^C$ and PrP$^{Sc}$ or, alternatively, for native or untreated PrP$^{Sc}$.

"Antigenic fragment" of a protein (e.g., a PrP protein) is meant a portion of such a protein which is capable of binding an antibody.

By "binds specifically" is meant high avidity and/or high affinity binding of an antibody to a specific polypeptide e.g., epitope of a protein, e.g., denatured PrP$^{Sc}$ or denatured A4β protein. Antibody binding to its epitope on this specific polypeptide is preferably stronger than binding of the same antibody to any other epitope, particularly those which may be present in molecules in association with, or in the same sample, as the specific polypeptide of interest e.g., binds more strongly to epitope fragments of a protein such as PrP$^{Sc}$ so that by adjusting binding conditions the antibody binds almost exclusively to an epitope site or fragments of a desired protein such as an epitope fragment exposed by denaturing of PrP$^{Sc}$ and not exposed on native PrP$^{Sc}$.

By "detectably labeled antibody", "detectably labeled anti-PrP" or "detectably labeled anti-PrP fragment" is meant an antibody (or antibody fragment which retains binding specificity), having an attached detectable label. The detectable label is normally attached by chemical conjugation, but where the label is a polypeptide, it could alternatively be attached by genetic engineering techniques. Methods for production of detectably labeled proteins are well known in the art. Detectable labels known in the art, but normally are radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labeling antibodies, and methods for using labeled antibodies are well known in the art (see, for example, Harlow and Lane, eds. (Antibodies: A Laboratory Manual (1988) Cold Spring Harbor Laboratory Press, Cold Spring Harbor, N.Y.)). Europium is a particularly preferred label.

Abbreviations used herein include:
CNS for central nervous system;
BSE for bovine spongiform encephalopathy;
CJD for Creutzfeldt-Jacob Disease;
FFI for fatal familial insomnia;
GdnHCl for Guanidine hydrochloride;
GSS for Gerstamnn-Strassler-Scheinker Disease;
Hu for human;
HuPrP for human prion protein;
Mo for mouse;
MoPrP for mouse prion protein;
SHa for a Syrian hamster;
SHaPrP for a Syrian hamster prion protein;
Tg for transgenic;
Tg(SHaPrP) for a transgenic mouse containing the PrP gene of a Syrian hamster;
Tg(HuPrP) for transgenic mice containing the complete human PrP gene;
Tg(ShePrP) for transgenic mice containing the complete sheep PrP gene;
Tg(BovPrP) for transgenic mice containing the complete cow PrP gene;
$PrP^{Sc}$ for the scrapie isoform of the prion protein;
$PrP^{C}$ for the cellular contained common, normal isoform of the prion protein;
PrP 27–30 or $PrP^{Sc}$ 27–30 for the treatment or protease resistant form of $PrP^{Sc}$;
$MoPrP^{Sc}$ for the scrapie isoform of the mouse prion protein;
MHu2M for a chimeric mouse/human PrP gene wherein a region of the mouse PrP gene is replaced by a corresponding human sequence which differs from mouse PrP at 9 codons;
Tg(MHu2M) mice are transgenic mice of the invention which include the chimeric MHu2M gene;
$MHu2MPrP^{Sc}$ for the scrapie isoform of the chimeric human/mouse PrP gene;
$PrP^{CJD}$ for the CJD isoform of a PrP protein;
$Prnp^{0/0}$ for ablation of both alleles of an endogenous prion protein gene, e.g., the MoPrP gene;
$Tg(ShaPrP^{+/0})81/Prnp^{0/0}$ for a particular line (81) of transgenic mice expressing SHaPrP, +/0 indicates heterozygous;
$Tg(HuPrP^{+/0})/Prnp^{0/0}$ for a hybrid mouse obtained by crossing a mouse with a human prion protein gene (HuPrP with a mouse with both alleles of the endogenous prion protein gene disrupted;
$Tg(MHu2M)/Prnp^{0/0}$ for a hybrid mouse obtained by crossing a mouse with a chimeric prion protein gene (MHu2M) with a mouse with both alleles of the endogenous prion protein gene disrupted;
TTR for transthyretin;
FVB for a standard inbred strain of mice often used in the production of transgenic mice since eggs of FVB mice are relatively large and tolerate microinjection of exogenous DNA relatively well;
[$PrP_\beta$]—concentration of prion protein in β-sheet conformation;
[$\beta A4_\beta$]—concentration of βA4 in β-sheet conformation;
[DRC]—concentration of a disease related conformation of a protein.

General Aspects of the Invention

The assay method comprises providing a sample suspected of containing a protein which assumes a first conformation and a second disease related conformation and is capable of detecting a disease conformation of the protein when present in a very low concentration relative to the concentration of other proteins and compounds including the non-disease conformation.

The assay methods disclosed allows one to isolate and detect the presence of a disease related conformation of a protein (e.g., $PrP^{Sc}$) present in a sample also containing the non-disease related conformation of the protein (e.g., $PrP^{C}$). The sample is treated (e.g., contacted with dispase) in a manner which hydrolyzes the $PrP^{C}$ and not the $PrP^{Sc}$. The hydrolyzation reaction is stopped (e.g., by the addition of EDTA). The treated sample is contacted with a binding partner (e.g., a labeled antibody which binds $PrP^{Sc}$) and the occurrence of binding provides and indication that $PrP^{Sc}$ is present. Alternatively the $PrP^{Sc}$ of the treated sample is denatured (e.g., contacted with guanadine) or unfolded. The unfolded $PrP^{Sc}$ is contacted with a binding partner (e.g., labeled 3F4) and the occurrence of binding indicates the presence of $PrP^{Sc}$ in the sample.

In accordance with any of the assay embodiments it is preferable to pre-treat the sample being tested to (1) remove as many contaminant proteins as possible; and (2) increase the concentration of disease related protein in the sample relative to the non-disease related conformation of the protein. For example, the initial sample can be chemically treated with a compound which preferentially degrades or denatures contaminant proteins and/or the relaxed, non-disease form of the protein and/or is exposed to antibodies which preferentially bind to (in order to remove) contaminants and/or non-disease conformation of the protein.

It may be possible to enhance further the sensitivity of various aspects of the invention by concentrating the disease conformation of a protein by adding a compound which selectively binds to the disease conformation to form a complex and centrifuging the sample to precipitate out the complex which is then tested in accordance with the methods described here. Specifics regarding such concentration methods are described in detail in our application Ser. No. 09/026,967 entitled "Process for Concentrating Protein with Disease-Related Conformation" now issued as U.S. Pat. No. 5,977,324 on Nov. 2, 1999.

The different embodiments of the assay of the invention described above are all "direct" types of immunoassays—meaning that the sample is directly assayed with the labeled antibody either with or without treatment to change the conformation of any disease related conformation proteins present in the sample. An "indirect" assay may also be used. For example, it may be desirable to enhance the number of disease related proteins in the sample (if any) by the use of a transgenic mouse and thereby enhance any signal obtained. To carry out these embodiments of the invention, the sample is first used to inoculate a transgenic mouse which has had its genome modified so that it will develop symptoms of disease when inoculated with proteins in the disease related conformation. After the mice are inoculated, a sufficient period of time is allowed to pass (e.g., 30 days) after which the transgenic animal is sacrificed and a sample such as homogenized brain tissue from the mouse is used in the direct assay described above. The present invention enhances the ability of transgenic mice to detect prions by shortening the period of time which must pass until a determination can be made as to whether the original sample included proteins in the disease related conformation. It would also be possible to use mice of the type disclosed and described in any of U.S. Pat. Nos. 5,565,186; 5,763,740; or 5,792,901 or to apply epitope tagged PrP as disclosed in U.S.

Pat. No. 5,750,361 to affinity purify the PrP$^{Sc}$ from the brain of a Tg mouse and thereafter apply the assay of the present invention. Without the present invention the mouse is inoculated and one must wait until the inoculated mouse actually demonstrates symptoms of the disease. Depending on the mouse, this can take several months or even years. Any of the assays of the present invention could be used with any transgenic mice such as those described above. The assay could be used well before the mouse developed symptoms of disease thereby shortening the time needed to determine if a sample includes infectious proteins.

The assay methodology of the present invention can be applied to any type of sample when the sample is suspected of containing a protein which occurs in at least two conformations. The protein must occur in one conformation which binds to known antibodies, antibodies which can be generated or other specific binding partners. The second conformation must be sufficiently different from the first conformation in terms of its ability to be hydrolyzed by compound (e.g., dispase). In its conceptually simplest form, the invention works best when a compound quickly and complete hydrolyzes the non-disease conformation of the protein without affecting the disease related conformation. However, in reality, a given protein may have more than two conformations. The protein may have more than one non-disease conformation and more than one disease related conformation, (Telling, et al., *Science* (1996)). The invention is still useful when multiple conformations of non-disease and disease forms of the protein exist—provided that (1) at least one non-disease conformation differs from at least one disease conformation in terms of its ability to be hydrolyzed by a compound.

As indicated above, the assay of the invention can be used to assay any type of sample for any type of protein, provided the protein includes a non-disease and a disease related conformation. However, the invention was particularly developed to assay samples for the presence of (1) PrP proteins and determine whether the sample included a PrP protein in its disease conformation, i.e., included $PrP^{Sc}$ (2) insoluble forms of βA4 associated with Alzheimer's disease and (3) transthyretin. Accordingly, much of the following disclosure is directed to using the immunoassay of the present invention to detect the presence of either $PrP^{Sc}$ (or to a lesser degree βA4 or transthyretin (TTR)) in a sample—it being understood that the same general concepts are applicable to detecting disease related conformations of a wide range of different types of proteins.

Europium labeled antibodies used (3F4) have a high binding affinity for $PrP^{C}$ (non-disease conformation) which comprises an α-helical rich conformation. The antibodies have a low binding affinity for $PrP^{Sc}$ (disease conformation) which comprises a β-sheet rich conformation. The IgG may be obtained from common monoclonal, polyclonal, or recombinant antibodies, typically recognizing the sequence 90–145 of $PrP^{C}$ and conformationally unfolded prion protein. Different conformations of recombinant prion protein were chemically crosslinked to polystyrene plates through a glutaraldehyde activation step. The relative affinities of the Eu-labeled IgG with α-helical, β-sheet, and random coil conformation of recombinant Syrian hamster prion protein corresponding to sequence 90–231 were determined by time-resolved, dissociation-enhanced fluorescence in a 96-well polystyrene plate format.

After the labeled antibodies have been provided with sufficient time, temperature and chemical conditions (e.g., pH) to bind to the appropriate proteins present in the respective portions the level of binding of the labeled antibody to protein is determined.

Once a labeled antibody has bound to its target detection may be difficult due to the low concentration of the target molecule in the sample. Different procedures can be used for detection.

Time-resolved, dissociation-enhanced fluorescence and more preferably dual wavelength, laser-driven fluorometers are particularly useful devices—see Hemmila et al., Boianalytical Applications of Labeling Technologies (eds. Hemmilä) 113–119 (Wallas Oy. Turku, Finland, 1995).

These devices make it possible to detect concentrations in an amount in the range of about $1\times10^{3}$ particles per ml or less. A high degree of sensitivity is preferred because in most samples the concentration of protein in the disease conformation will be very low. For example, the non-disease conformation of the protein might be present in an amount of about $1\times10^{8}$ particles/ml while the disease conformation of the protein is only present in an amount of $1\times10^{4}$ particles/ml.

The assay can be used to test for the presence of the disease conformation of a given protein within any type of sample. Some of the most typical samples to be tested include pharmaceuticals which include components which are derived from living mammals or use materials derived from living mammals in their processing. It would also be desirable to test organs for transplantation and food items such as beef which was suspected of containing infectious prions. The invention could be used for testing for the presence of the disease conformation of one or more types of proteins such as infectious $PrP^{Sc}$ in pharmaceuticals, cosmetics, biopsy or autopsy tissue, brain, spinal cord, peripheral nerve, muscle, cerebrospinal fluid, blood and blood components, lymph nodes, and in animal or human-derived cultures infected or potentially infected by disease forms of proteins such as prions. The brains of cows suspected of being infected with prions (i.e., $BoPrP^{Sc}$) could be tested to determine if the cows can be safely used for human consumption.

Treatment—General

An assay of the invention can use all or any of three basic types of treatment which are defined above. The treatments are (1) pretreatment, (2) unfolding treatment and (3) hydrolysis treatment. In general the conditions for pretreatment are gentle, those for unfolding treatment moderate and those for hydrolysis treatment are harsh. Each type of treatment can employ the same means (e.g. proteases, time, pH, temperature, etc.) but employs each to a different degree, e.g. higher concentration, longer time, higher temperature. However, the hydrolysis treatment must employ a compound which selectively hydrolyzes only the non-disease conformation and not the disease conformation.

Pretreatment

Before carrying out treatment or antibody testing of the sample it may be desirable to subject the sample to pretreatment. The pretreatment is carried out in order to destroy or remove unrelated proteins as well as some of the non-disease form of the protein present within the sample. Examples of pretreatment methodology include producing a column which includes antibodies bound to support surfaces which antibodies bind to the non-disease conformation of the protein thereby removing as much of the non-disease conformation of the proteins possible. Antibodies which bind unrelated but common proteins can also be used. Alternatively, the sample can be subjected to physical treatment such as long term hydrostatic pressure or temperature alone or in combination with chemicals such as acids or alkalines as indicated above to destroy proteins present in the sample which proteins are not related to those being assayed for or are in the non-disease conformation. In some instances proteins in the non-disease and disease conformation will be destroyed. However, a higher relative percentage of the proteins in the non-disease conformation will be destroyed because these proteins are initially in a looser conformation which is more vulnerable to destruction. Thus, the pretreatment methodology results in a sample which includes a relatively lower concentration of the non-disease conformation of the protein relative to the concentration of the disease conformation of the protein. Further, the pretreated sample will have a lower concentration of unrelated proteins. This increases the sensitivity of the assay making it possible to detect lower concentrations of the disease conformation of the protein. Removal of proteins is preferred over destruction of such in that destruction will decrease sensitivity if the disease conformation is destroyed. A particularly useful pretreatment method is disclosed in U.S. Pat. No. 5,977,324 on Nov. 2, 1999.

Unfolding Treatment

The unfolding treatment denatures the protein but does not hydrolyze proteins of interest and can include exposing the proteins to any physical and/or chemical means which causes the protein which is originally present in a tightened, disease related conformation (e.g., $PrP^{Sc}$) to assume a more relaxed conformation which has a higher degree of binding affinity for any binding partner such as antibodies (e.g., expose an N-terminal epitope of $PrP^{Sc}$). In general, the unfolding treatment involves subjecting the protein to some means which causes epitopes on the protein which were not previously exposed or partially exposed to become exposed or become more exposed so that an antibody or other binding partner can more readily bind to the newly exposed epitope.

Methods used for unfolding treatment may include: (1) physical, such as hydrostatic pressure or temperature, (2) chemical, such as acidic or alkaline pH, chaotropic salts, denaturing detergents, guanidine hydrochloride and proteinases such as Proteinase K and (3) combinations of above.

The treatment time will vary depending on the treatment used but should be carried out for sufficient time to obtain the desired effect, e.g. for unfolding treatment to expose new binding sites but not so long as to completely denature or hydrolyze the protein. When carrying out unfolding treatment on PrP proteins without chemical treatment the temperature is raised to about 40° C. to about 80° C. for a time sufficient to obtain the desired amount of unfolding of $PrP^{Sc}$. The temperature can be lower and the time shorter if the pH is raised to 12 or 13.

Hydrolysis Treatment

The hydrolysis treatment is a lytic treatment which is the most important treatment method used in one embodiment of the assays of the invention. After a sample has been subjected to the pretreatment treatment it is subjected to the hydrolysis treatment. This treatment will destroy or hydrolyze all or substantially all protein in the sample which is in the non-disease conformation and not hydrolyze the protein in the disease conformation. The hydrolysis treatment is prferably via an enzyme such as a hydrolase that acts on peptide bonds, preferably a neutral protease, more preferably a metalloendopeptidase, and most preferably dispase or leucostoma peptidase A. The proteases used in the method of the invention may be used alone, in combination, or in conjunction with enzymes having similar but distinct activity such as a carbohydrase, e.g. collagenase, amylase, or alkaline serine protease. The concentration of the treating compounds as well as the time and temperature will vary with the protein being treated and end result to be obtained. For example, with PrP the treatment is carried out to hydrolyze all or substantially all non-$PrP^C$ present, but not hydrolyze $PrP^{Sc}$ present. The object of this treatment is to hydrolyze as much non-disease protein as possible (preferably all) while hydrolyzing as little (preferably none) disease related protein as possible. The treatment is preferably designed such that it can be quickly and completely stopped at any given time. For example, hydrolysis of $PrP^C$ with dispase or other related proteases can be stopped by adding EDTA.

The following list of enzymes are preferred compounds of the method of the invention:

| Enzyme | Biological Source |
|---|---|
| Dispase | Bacillus polymyxa |
| Atrolysin A, B, C, E and F | Western diamondback rattlesnake Crotalus atrox |
| Envelysin | Various member of the class Echinoidea |
| Thimet oligopeptidase | Related to Saccharolysin from Saccharomyces cerevisiae. |
| Matrilysin | Ratuterus |
| Vibriolysin | Vibrio proteolyticus (formerly Aeromonas proteolytica) |
| Coccolysin | Streptococcus thermophilus |
| Mycolysin | Streptomyces griseus |
| Meprin A | ratus and mus kidney and intestinal brush border |
| Astacin | The crayfish Astacus fluviatilis |
| Aureolysin | Staphylococcus aureus |
| Leishmanolysin | Various species of Leishmania protozoans |
| Peptidyl-Asp Metalloendopeptidase | Psuedomonas fragi |
| Autolysin | Chlamydomonas reinhardtii |
| Deuterolysin | Penicillium roqueforti; species variants include Penicillium caseicolum, Aspergillus sojae, and Aspergillus oryzae. |
| Bothrolysin | Venom of jararaca snake Bothrops jararaca |
| Stromelysin 1 and 2 | Human rheumatoid synovial fibroblasts |
| Bacillolysin | Bacillus subtilis; species variants include Bacillus, amyloliquefaciens, Bacillus megaterium, Bacillus mesentericus, Bacillus cereus, and Bacillus stearothermophilus |
| Thermolysin | Bacillus thermoproteolyticus; species variants include Micrococcus caseolyticus and Aspergillus oryzae. |
| Aeromonolysin | Honey fungus Armillaria mellea |
| Leucolysin | Venom of the western cottonmouth moccasin snake, Agkistrodon piscivorus |
| Mycolysin | Streptomyces griseus, Streptomyces naraensis, and Streptomyces cacaoi |
| Pseudolysin | Psuedomonas aeruginosa |
| Peptidyl-Lys Metalloendopeptidase | Pseudomonas fragi |

-continued

| Enzyme | Biological Source |
|---|---|
| Aureolysin | *Staphylococcus aureus* |
| Neprilysin | Widely distributed in mammal tissues, including brain, liver and lung; abundant in kidney brush border membrane |
| β-lytic Metalloendopeptidase | *Achromobacter lyticus* and *Lysobacter enzymogenes* |
| Peptidyl-Asp Metalloendopeptidase | *Pseudomonas fragi* |
| Ophiolysin | Venom of the King Cobra *Ophiophagus hannah.* |
| Pitrilysin | *Escheria coli* |
| Insulysin | mammals and *Drosophila melanogasters* |
| Serralysin | *Pseudomonas aeruginosa*; species variants include *Escheria freundii, Serratia marcescens,* and *Erwinia chrysanthemi.* |

The method of the invention is not limited to these enzymes, and thus other enzymes predicted by those skilled in the art to function in the method of the invention may be used.

Binding Proteins to Support Surfaces

The method of chemical or affinity coupling of PrP protein to the plastic support are generally described in available literature and may vary. The antibodies used in the diagnostic assay are polyclonal, monoclonal or recombinant Fab and need to be species specific with preferential binding to the native $PrP^C$ or denatured form of $PrP^{Sc}$ with preferably at least 4-fold lower reactivity with infectious $PrP^{Sc}$, assuming the same amount of the antigen.

Using the Assay to Detect Prions ($PrP^{Sc}$)

One aspect of the invention is a two step process to diagnose prion disease by quantitatively measuring the native infectious form of $PrP^{Sc}$ protein in sample material or in the brains of susceptible animals inoculated with such material. The sample is preferably pretreated to remove as much unrelated and non-disease protein as possible. The pretreated sample is first subjected to hydrolysis treatment and then crosslinked to the plastic support.

To measure the concentration of $PrP^{Sc}$ when it is much less than $PrP^C$, the detection system has to have extreme sensitivity and a linear range of at least $10^4$. The assay described herein can readily detect $PrP^{Sc}$ at a concentration of (approximately) 50 pg/ml using Europium-labeled IgG. Assuming $10^5$–$10^6$ $PrP^{Sc}$ molecules per $ID_{50}$ unit the present assay can readily detect $5 \times 10^2$–$5 \times 10^3$ $ID_{50}$ units per ml.

The assay can detect $PrP^{Sc}$ in mixtures (by direct method) where the concentration of $PrP^{Sc}$ is less than 1% of the concentration of $PrP^C$. Additional sensitivity can be achieved by immunoprecipitation, using a sandwich format for a solid state assay, differential centrifugation with detergent extraction to remove $PrP^C$, the indirect transgenic animal method or combinations of these methods. A conservative estimate is that such procedures should allow measurement of between 5 and 50 $ID_{50}$ units per ml or less conservatively to measure between 0.1 and 0.01 $ID_{50}$ units per ml. Such measurements would provide a rapid, "positive" means of establishing biological sterility which is the "absence" of infectivity.

Antibodies

Method of generating antibodies are generally known to those skilled in the art. In that the disease form is often in a tighter configuration than the non-disease form, with less epitopes exposed, one can readily generate antibodies which bind only to the non-disease form of the protein or the treated disease form. For example, antibodies detecting treated forms of $PrP^{Sc}$ protein and $PrP^C$ protein may be generated by immunizing rabbits or mice with α-helical conformations of recombinant PrP, native $PrP^C$ from animal brains, synthetic peptides in α-helical or random coil conformations, or against denatured $PrP^{Sc}$ or PrP 27–30. Only antibodies with affinity at least 4 fold higher for $PrP^C$ (or denatured conformation of $PrP^{Sc}$ of the same species) as compared to their affinity for $PrP^{Sc}$ should be selected. The method of antibody generation, purification, labeling and detection may vary.

The IgG or Fab's may be purified from different sources by affinity HPLC using protein A column and Size exclusion HPLC. The purified antibodies may be labeled with Europium and detected by time resolved fluorescence. The antibody binding to different conformations of PrP protein may be measured by time-resolved, dissociation-enhanced fluorescence. However, the system of detection of PrP-bound IgG on solid support in situ or in solution may vary. Further, it is possible to use direct or indirect immunological methods including direct radiolabels, fluorescence, luminescence, avidin-biotin amplification, or enzyme-linked assays with color or luminescent substrates.

An antibody which can be used in the invention is disclosed in U.S. Pat. No. 4,806,627, issued Feb. 21, 1989, disclosing monoclonal antibody 263K 3F4, produced by cell line ATCC HB9222 deposited on Oct. 8, 1986, which is incorporated herein by reference. The cell line producing the antibody can be obtained from the American Type Culture Collection, 10801 University Boulevard, Manassas, Va. 20110-2209.

In general, scrapie infection fails to produce an immune response, with host organisms being tolerant to $PrP^{Sc}$ from the same species. Antibodies which bind to either $PrP^c$ or $PrP^{Sc}$ are disclosed in WO97/10505, published Mar. 20, 1997. Any antibody binding to $PrP^c$ and not to $PrP^{Sc}$ can be used, and those skilled in the art can generate such using known procedures, e.g., see methods of producing page display antibody libraries in U.S. Pat. No. 5,223,409. Polyclonal anti-PrP antibodies have though been raised in rabbits following immunization with large amounts of formic acid or SDS-denatured SHaPrP 27–30 [Bendheim, Barry et al. (1984) *Nature* 310:418–421; Bode, Pocchiari et al. (1985) *J Gen Virol* 66:2471–2478; Safar, Ceroni et al. (1990) *Neurology* 40:513–517]. Similarly, a handful of anti-PrP monoclonal antibodies against PrP 27–30 have been produced in mice [Barry and Prusiner (1986) *J Infect Dis* 154:518–521; Kascsak, Rubenstein et al. (1987) *J Virol* 61:3688–3693]. These antibodies were generated against formic acid- or SDS-denatured PrP 27–30 and are able to recognize native $PrP^C$ and treated or denatured $PrP^{Sc}$ from both SHa and humans equally well, but do not bind to MoPrP. Not surprisingly, the epitopes of these antibodies were mapped to regions of the sequence containing amino acid differences between SHa- and MoPrP [Rogers, Yehiely et al. (1993) *Proc Natl Acad Sci USA* 90:3182–3186].

It is not entirely clear why many antibodies of the type described in the above cited publications will bind to $PrP^C$ and treated or denatured $PrP^{Sc}$ but not to native $PrP^{Sc}$. Without being bound to any particular theory it is suggested that such may take place because epitopes which are exposed when the protein is in the PrP$^C$ conformation are unexposed or partially hidden in the PrP$^{Sc}$ configuration—where the protein is relatively insoluble and more compactly folded together.

For purposes of the invention an indication that no binding occurs means that the equilibrium or affinity constant $K_a$ is $10^6$ 1/mole or less. Further, binding will be recognized as existing when the $K_a$ is at $10^7$ 1/mole or greater, preferably $10^8$ 1/mole or greater. The binding affinity of $10^7$ 1/mole or more may be due to (1) a single monoclonal antibody (i.e., large numbers of one kind of antibodies) or (2) a plurality of different monoclonal antibodies (e.g., large numbers of each of five different monoclonal antibodies) or (3) large numbers of polyclonal antibodies. It is also possible to use combinations of (1)–(3). Selected preferred antibodies will bind at least 4-fold more avidly to the treated or denatured PrP$^{Sc}$ forms of the protein when compared with their binding to the native conformation of PrP$^{Sc}$. The four fold differential in binding affinity may be accomplished by using several different antibodies as per (1)–(3) above and as such some of the antibodies in a mixture could have less than a four fold difference.

A variety of different types of assays of the invention may be used with one or more different antibodies. Those skill in the art will recognize that antibodies may be labeled with known labels and used with currently available robotics, sandwich assays, electronic detectors, flow cytometry, and the like.

Diseases Associated with Insoluble Proteins

Much of the disclosure and the specific examples provided herein relate to the use of the assay in connection with determining the presence of $PrP^{Sc}$ in the sample. However, as indicated above, the assay of the invention can be applied to determining the presence of any protein which assumes two different conformational shapes, one of which is associated with the disease. The following is a non-limiting list of diseases with associated insoluble proteins which assume two or more different conformations.

| Disease | Insoluble Proteins |
|---|---|
| Alzheimer's Disease | APP, Aβ peptide, α1-antichymotrypsin, tan, non-Aβ component |
| Prion diseases, Creutzfeld Jakob disease, scrapie and bovine spongeform encephalopathy | $PrP^{Sc}$ |
| ALS | SOD and neurofilament |
| Pick's disease | Pick body |
| Parkinson's disease | Lewy body |
| Diabetes Type 1 | Amylin |
| Multiple myeloma--plasma cell dyscrasias | IgGL-chain |
| Familial amyloidotic polyneuropathy | Transthyretin |
| Medullary carcinoma of thyroid | Procalcitonin |
| Chronic renal failure | $\beta_2$-microglobulin |
| Congestive heart failure | Atrial natriuretic factor |
| Senile cardiac and systemic amyloidosis | Transthyretin |
| Chronic inflammation | Serum amyloid A |
| Atherosclerosis | ApoA1 |
| Familial amyloidosis | Gelsolin |

It should be noted that the insoluble proteins listed above each include a number of variants or mutations which result in different strains which are all encompassed by the present invention. Known pathogenic mutations and polymorphisms in the PrP gene related to prion diseases are given below and the sequences of human, sheep and bovine are given in U.S. Pat. No. 5,565,186, issued Oct. 15, 1996.

MUTATION TABLE

| Pathogenic human mutations | Human Polymorphisms | Sheep Polymorphisms | Bovine Polymorphisms |
|---|---|---|---|
| 2 octarepeat insert | Codon 129 Met/Val | Codon 171 Arg/Glu | 5 or 6 octarepeats |
| 4 octarepeat insert | Codon 219 Glu/Lys | Codon 136 Ala/Val | |
| 5 octarepeat insert | | | |
| 6 octarepeat insert | | | |
| 7 octarepeat insert | | | |
| 8 octarepeat insert | | | |
| 9 octarepeat insert | | | |
| Codon 102 Pro-Leu | | | |
| Codon 105 Pro-Leu | | | |
| Codon 117 Ala-Val | | | |
| Codon 145 Stop | | | |
| Codon 178 Asp-Asn | | | |
| Codon 180 Val-Ile | | | |
| Codon 198 Phe-Ser | | | |
| Codon 200 Glu-Lys | | | |
| Codon 210 Val-Ile | | | |
| Codon 217 Asn-Arg | | | |
| Codon 232 Met-Ala | | | |

It should also be noted that such proteins have two different 3-dimensional conformations with the same amino acid sequence. One conformation is associated with disease characteristics and is generally insoluble whereas the other conformation is not associated with disease characteristics and is soluble. The methodology of the present invention is not limited to the diseases, proteins and strains listed.

Detecting the β-Sheet Form of β4

One aspect of the invention involves a two step process to diagnose Alzheimer's disease based on the presence of a constricted form of a protein (βA4 amyloidosis) by quantitatively measuring β-sheet form of βA4 protein in sample material, e.g., in the brain or body fluids. The sample is divided into two aliquots. The first aliquot is crosslinked to a solid plastic (long chain polymeric material) support in native conformation through a chemical activation step under the nondenaturing conditions. The second portion of the sample is first subjected to unfolding treatment and then crosslinked to the plastic support. Both portions of the sample material react in situ with the labeled antibodies that preferentially recognize soluble βA4 or unfolding treatment βA4 of the human or a given animal species. The amount of the antibody bound to unfolded or native conformations of βA4 protein is recorded by the signal of the labeled secondary antibody. The excess of the signal obtained with the unfolding treated sample compared to that expected change in the signal obtained with the native α-helical conformation of βA4 protein is the measure of the amount of β-sheet structured βA4 in the original sample. The formula developed for calculation of βA4 content is provided above in connection with the calculation of $PrP^{Sc}$ content.

The diagnosis of βA4 amyloidosis (Alzheimer's disease) is established by three procedures: (1) measurement of denatured sample alone and by detecting the increase in the total βA4 amount (concentration) in the examined sample above the background levels of soluble βA4 obtained from normal controls; (2) calculation of the ratio between unfolding treated versus native signal for a given antibodies (protein index)—for example values higher than 2 for monoclonal antibody 6F3D and europium labeled secondary antibody; (3) evaluation of the change of the denatured sample signal over that expected change in the signal for α-helical conformation of βA4 as a measure of the amount of infectious β-sheet structured βA4 in the original sample. The formula developed for calculation of βA4 content is provided above. The particular strain of βA4 can also be determined using the same methodology described above to determine the strain of $PrP^{Sc}$ in a sample.

The invention provides a direct diagnostic method for detecting the presence pathogenic forms of βA4 protein in pharmaceuticals, biopsy or autopsy tissue, brain, spinal cord, peripheral nerves, muscle, cerebrospinal fluid, blood and blood components, lymph nodes, and in animal- or human-derived cultures expressing or potentially expressing βA4 protein. The invention also makes it possible to follow the α-helix-to-β-sheet conformational transition of βA4 protein, or its fragments of synthetic or recombinant origin, and to provide a method to screen compounds for their ability to stabilize the normal soluble conformation of βA4 protein and thus prevent conversion into pathogenic insoluble and β-sheet-structured βA4 protein.

Typical methods of sample denaturation include: (1) physical, such as hydrostatic pressure or temperature, (2) chemical, such as acidic or alkaline pH, chaotropic salts, or denaturing detergents, and (3) combination of above. Methods of chemical or affinity coupling of βA4 protein to a plastic support are described in available literature and may vary. Antibodies used in the diagnostic assay may be polyclonal, monoclonal or recombinant Fab and must be species specific with preferential binding to the soluble or denatured form of βA4 with preferably at least a 2-fold difference in reactivity between α-helical and β-sheet structured βA4, assuming the same amount of antigen.

Methods of sample attachment to the plastic support may vary and may be covalent or non-covalent as described in available literature. The sensitivity of the assay described in the examples may be increased by using high-affinity antibodies, sandwich formate, immunoprecipitation, or differential centrifugation. However, only the antibodies with an affinity at least a 2 fold for unfolding treated as compared to the native β-sheet conformation of βA4 of the same species shall be used for the diagnostic assay. Methods of antibody generation, purification, labeling and detection may vary. The antibody binding to different conformations of βA4 protein was measured by time-resolved, dissociation-enhanced fluorescence. However, the system of detection of βA4-bound IgG on solid support in situ or in solution may vary and may use direct or indirect immunological methods including direct radiolabels, fluorescence, luminescence, avidin-biotin amplification, or enzyme-linked assays with color or luminescent substrates.

EXAMPLES

The following examples are put forth so as to provide those of ordinary skill in the art with a complete disclosure and description of how to make and use assays of the present invention, and are not intended to limit the scope of what the inventors regard as their invention, nor are they intended to represent or imply that the experiments below are all of or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1

Detection of $PrP^{Sc}$ in Hamster Brain

To determine the levels of $PrP^{Sc}$ in affected hamsters, a prion infected hamster and a normal hamster were each sacrificed and their brains removed. A 10% (w/v) homogenate of each of the brains was prepared by dispersing the brain tissue in PBS. The brain homogenate was then subjected to a low speed centrifugation of 500×g for 15 minutes to separate the suspended proteins from unwanted cellular debris. The total protein concentration of the supernatant (S1) was measured using a BCA Protein Assay (Pierce) and the concentration of each brain homogenate was adjusted with PBS to 3.5 mg/ml. A portion of the homogenate was saved to serve as a control of total brain proteins.

The metalloendopeptidase dispase (Worthington) was added to the remainder of each sample at an enzyme to protein ratio of 1:35. The homogenates were digested with 100 µg/ml dispase for 60 min at 37° C. in the presence of either 0.15% Zwittergent 3–12 (Calbiochem), or 0.2% or 2% of sodium dodecyl sarcosinate (Sarkosyl). A sample without the dispase was also placed at 37° C. to serve as a digestion control. Following digestion the dispase was inactivated by the addition of 50 mM EDTA.

As a control, Proteinase K digestion was done on each untreated S1 sample with 20 µg/ml at a ratio of enzyme to protein of 1:50 (Bolton, 1982) in the presence of either 0.15% Zwittergent, 0.2% or 2% Sarkosyl. These reactions were terminated by the addition of 2 mM PMSF.

The digested samples were centrifuged at 100,000×g for 1 hour. The pellet containing all the insoluble proteins was resuspended in a minimal volume of PBS and 0.15% Zwittergent. Subsequently, both the digested samples and the whole brain homogenate samples were sonicated in a water bath sonicator for 20 minutes to denature the protein remaining after digestion.

Each sample was then analyzed for PrP protein content by immunoblot. A 100 µl aliquot of each sample was placed in a 1.5 ml eppendorf tube with an equal volume of sample loading buffer (1×=50 mM Tris Cl, pH 6.8; 100 mM DTT; 2% SDS; 0.1% bromophenol blue; and 10% glycerol). In addition, an aliquot of b-mercaptoethanol can be added to ensure denaturation of the proteins on the gel. The samples were run on a 10% polyacrylamide gel, molar ratio of bisacrylamide:acrylamide of 1:29, for 15 V/cm for about 4 hours. The samples were each boiled for 10 minutes, and 15 µl of each sample was loaded onto the gel. For a more detailed description of protein separation via PAGE, see Schägger and Von Jagow, *Nature* 166:368–379 (1987) and Laemmli, U. K. (1970) *Nature* 227, 680–685, which are both incorporated herein in their entirety.

The gel was removed from the PAGE apparatus, and transferred onto uncharged nylon (Amersham) using an electroblotting apparatus. The gel and the nylon were sandwiched between pieces of Whatman 3MM paper soaked in a transfer buffer containing Tris, glycine, SDS and methanol. The sandwich was placed between graphite plate electrodes, with the nylon on the anodic side. A current of 0.65 mA/sq. cm was applied for 1.5–2 hours. Following transfer, the gel was stained with coomassie blue to be sure the transfer was complete.

The nylon filter was placed in a heat-sealable plastic bag, and 0.1 ml of blocking solution were added per square cm of filter. The blocking solution contained 5% (w/v) nonfat dry milk (Carnation); 0.01% antifoam A; and 0.02% sodium azide in PBS. After 1 hour shaking at room temperature, the monoclonal antibody 3F4 was added in a 1:100 dilution, and the filter incubated for 2–4 hours at 4° C. with gentle agitation on a platform shaker. Following incubation, the blocking solution and antibody were removed, and the filter washed three times.

The filter was incubated with an anti-Ig secondary antibody in blocking solution for 1–2 hours at room temperature. The secondary antibody was radiolabeled to allow immunoblot detection. For the radiolabeled $I^{125}$ probe, approximately $10^4$ cpm of the reagent was added per square centimeter of filter. After incubation, the filter was washed several times in PBS, each wash being about 10 minutes in length. The filter was placed in a cassette with a piece of Xomat X-ray film (Kodak) at −70° C.

The results of the immunoblot were as follows:
lane 1 normal hamster S1
Result: strong band at about 33–35 Kd
lane 2 normal hamster S1 at 37° C.
Result: strong band at about 33–35 Kd
lane 3 normal hamster S1 digested with 100 g/ml dispase, 0.15% Zwittergent
Result: no band
lane 4 normal hamster S1 digested with 100 μg/ml dispase, 0.2% Sarkosyl
Result: no band
lane 5 normal hamster S1 digested with 100 g/ml dispase, 2% Sarkosyl
Result: no band
lane 6 normal hamster S1 digested with 20 μg/ml protein kinase, 0.2% Sarkosyl
Result: no band
lane 7 normal hamster S1 digested with 20 μg/ml protein kinase, 2% Sarkosyl
Result: no band
lane 8 prion-infected hamster S1
Result: strong band at about 33–35 Kd
lane 9 prion-infected hamster S1 at 37° C.
Result: strong band at about 33–35 Kd
lane 10 prion-infected hamster S1 digested with 100 μg/ml dispase, 0.15% Zwittergent
Result: very strong band at about 33–35 Kd
lane 11 prion-infected hamster S1 digested with 100 μg/ml dispase, 0.2% Sarkosyl
Result: very strong band at about 33–35 Kd
lane 12 prion-infected hamster S1 digested with 100 μg/ml dispase, 2% Sarkosyl
Result: very strong band at about 33–35 Kd
lane 13 prion-infected hamster S1 digested with 20 μg/ml protein kinase, 0.2% Sarkosyl
Result: very strong band at about 27–30 Kd
lane 14 prion-infected hamster S1 digested with 20 μg/ml protein kinase, 2% Sarkosyl
Result: very strong band at about 27–30 Kd These results showed that normal hamster brain $PrP^C$ was not detected after digestion with Dispase or Proteinase K, while samples from the prion infected brain showed a very strong signal of protease resistant protein. The prion infected samples digested with proteinase K showed an expected shift in the size of the molecular weight corresponding to the digestion of the n-terminus of the protein. The digestion with Dispase showed no shifting in the molecular weight. This finding showed that the Dispase is selective for the normal conformation of the protein.

Example 2

Detection of $PrP^{Sc}$ in Mouse Brain

To determine the levels of $PrP^{Sc}$ in affected mice, a prion infected mouse and a normal mouse are each sacrificed and their brains removed. A 10% (w/v) brain homogenate from normal and prion infected mice is prepared in PBS. After a low speed centrifugation at 500×g for 15 min, the total protein in the supernatant (S1) is measured using spectrophotometric assays, and the concentration is adjusted to 2.5 mg/ml with PBS.

The samples are digested with 500 U/ml Leucolysin for 45 min at 37° C. in the presence of 2% Sarkosyl. The digestion is stopped by the addition of 50 mM EDTA. An aliquot of the proteins obtained in S1 both before and after the leucolysin digestion are electrophoresed at 4° C. on an 8% polyacrylamide slab gel as described in the Laemmli reference but in the absence of SDS and 2-mercaptoethanol. This allows the nondenatured proteins to migrate through the polyacrylamide while preserving the native structure of the protein. Once immobilized in the polyacrylamide, the proteins of the gel are then transferred to nitrocellulose for protein detection. Transfer may occur as in Example 1, or a semi-dry transfer apparatus may be used (Reference Maniatis).

The digested and undigested sample of both infected and normal mouse are detected in Western blot as described in Example 1, but using a monoclonal antibody that recognizes the native $PrP^{Sc}$ form of the protein. Such antibodies are described in U.S. Ser. No. 08/804,536, now issued as U.S. Pat. No. 5,891,641 on Apr. 6, 1999, Ser. Nos. 09/026,957 and 09/151,057, each of which is incorporated herein by reference in their entirety. Preferably, the antibody used is the $PrP^{Sc}$-specific antibody R1. The antibodies are added at a concentration of about 1:100 to 1:200, depending on the antibody used and the amount of protein predicted to be immobilized on the nitrocellulose.

The nitrocellulose is placed in a heat-sealable plastic bag, and 0.1 ml of blocking solution is added per square cm of filter. The blocking solution contains 5% (w/v) nonfat dry milk (Carnation); 0.01% antifoam A; and 0.02% sodium azide in PBS, and Tween 20 added to a final concentration of 0.02%. The Tween 20 is a gentle detergent that further aids in reducing the background. After 1 hour shaking at room temperature, the R1 antibody is added in a 1:100 dilution, and the filter is incubated for 2–4 hours at 4° C. with gentle agitation on a platform shaker. Following incubation, the blocking solution and antibody are removed, and the filter is washed three times.

The filter is incubated with an anti-Ig secondary antibody in blocking solution for 1–2 hours at room temperature. The secondary antibody is enzyme-conjugated with horseradish peroxidase to allow immunoblot detection. The secondary antibody is added at a much more dilute level than the primary antibody, from 1:500 to 1:2000 dilution. After incubation, the filter is washed several times in PBS, each wash being about 10 minutes in length. The filter is then placed in a cassette with a piece of Xomat X-ray film (Kodak) at −70° C.

The resulting blot will have a band corresponding to $PrP^{Sc}$ in the sample of the treated, prion infected mouse brain, both before and after digestion with Leucolysin. The sample of the normal mouse brain protein will show a low level band due to background binding of the PrP$^{Sc}$. The lane with the normal brain sample subjected to hydrolysis with Leucolysin, however, will not have a detectable band, since the Leucolysin will have hydrolysed the PrP protein in the sample.

Example 3

Detection of PrP$^{Sc}$ in Cow Brain

A 10% (w/v) brain homogenate from normal and prion infected cows is resuspended in 1 L of 25 mM Tris.HCl, pH 8.0, 5 mM EDTA (buffer A). This is centrifuged at 10,000×g for 20 min, and the supernatant containing soluble periplasmic proteins is discarded. The pellet is resuspended in 1 L of buffer A, passed through a cell disrupter twice (Microfluidics International, model MF110), and centrifuged at 30,000×g for 1 h, after which the supernatant is discarded and the pellet is washed once in buffer A and centrifuged again at 30,000×g for 1 hour. At this stage the pellet could be stored at −20° C. prior to hydrolysis.

The β-Lytic Metalloendopeptidase digestion is done at an enzyme to protein ratio of 1:40. The protein is digested with 100 Φg/ml β-Lytic Metalloendopeptidase (Sigma) for 75 min at 40EC in a buffered pH 8.0 solution containing 0.2% Sarkosyl. The digestion is stopped by the addition of 50 mM EDTA. Following the hydrolysis of the PrP$^C$ conformation of the prion protein, the PrP$^{Sc}$ can be denatured to allow the 3F4 antibody to recognize its epitope. Both the normal and prion infected samples are treated with a denaturation solution of 6M guanidine HCl. The denaturation solution is prepared by diluting 10× buffer (250 mM HEPES (pH 7.9); 30 mM MgCl2; 40 mM KCl) with five volumes of distilled water. An appropriate amount of the guanidine HCl is added, and the solution is brought to 1× using distilled water. Finally, dithiothreitol is added to a final concentration of 1 mM. The hydrolyzed samples are subjected to treatment with the denaturation solution for 30 minutes at 4EC.

The samples are then loaded onto 10% polyacrylamide gels as described in Example 1, and transferred to nylon membrane. The nylon membrane is placed in a heat-sealable plastic bag, and 0.1 ml of blocking solution is added per square cm of filter. The blocking solution contains 5% (w/v) nonfat dry milk (Carnation) and 0.02% sodium azide in PBS. After 1 hour shaking at room temperature, the monoclonal antibody 3F4 is added in a 1:200 dilution, and the filter incubated for 2–4 hours at 4° C. with gentle agitation on a platform shaker. Following incubation, the blocking solution and antibody are removed, and the filter washed three times. The filter is incubated with an anti-Ig secondary antibody in blocking solution for 1–2 hours at room temperature, the filter washed several times in PBS, and placed in a cassette with a piece of Xomat X-ray film (Kodak) at −70° C.

The determination of prion infection is based on a comparison of recognition of PrP in the normal and infected samples. The lanes containing unhydrolyzed S1 should contain relatively similar amounts of PrP protein recognized by the 3F4 antibody. The lanes containing the hydrolyzed, guanidine HCl-treatded samples will allow the detection of PrP$^{Sc}$ in the infected sample, since the only form left after the hydrolysis is the PrP$^{Sc}$ form. The ratio of signal between the hydrolyzed and unhydrolyzed sample from the infected cow will determine the percentage of PrP that is in the PrP$^{Sc}$ conformation. The hydrolyzed normal cow sample will further serve as a control that the hydrolysis of the PrP$^C$ conformation was complete.

Example 4

Comparison of 3F4 and R1 Staining of a Sample

To determine the levels of PrP$^{Sc}$ in affected mice, a prion infected mouse and a normal mouse are each sacrificed and their brains removed. A 10% (w/v) homogenate of each of the brains was prepared by dispersing the brain tissue in PBS. The brain homogenate was then subjected to a low speed centrifugation of 500×g for 15 minutes to separate the suspended proteins from unwanted cellular debris. The total protein concentration of the supernatant (S1) was measured using a BCA Protein Assay (Pierce) and the concentration of each brain homogenate was adjusted with PBS to 3.5 mg/ml. A portion of the homogenate was saved to serve as a control of total brain proteins.

Each sample was then analyzed for PrP$^{Sc}$ and PrP$^C$ protein content by immunoblot. Two 100 μl aliquot of each sample was processed and electrophoresed at 4° C. on an 8% polyacrylamide slab gel as described in Example 2, i.e. under nondenaturing conditions. The gel is loaded with two lanes of sample from the affected mouse and two lanes of sample from the control mouse, and preferable one lane of each is run on one side of the gel, one lane of each on the other side of the gel, with wells containing no sample separating the two sides. The gel is run and transferred to nylon as per Example 1.

Following transfer, the nylon is cut to separate the nylon into two separate blots, each containing a lane of affected and a lane of control sample. Each nylon filter is placed in a heat-sealable plastic bag, and 0.1 ml of blocking solution is added per square cm of filter. The blocking solution contains 5% (w/v) nonfat dry milk (Carnation) and 0.02% sodium azide in PBS. After 1 hour shaking at room temperature, antibody 3F4 is added to one blot in a 1:200 dilution, and antibody R1 is added to the other blot in a 1:200 dilution, and the filter is incubated for 2–4 hours at 4° C. with gentle agitation on a platform shaker. Following incubation, the blocking solution and antibody are removed, and each filter washed three times.

The secondary antibody is properly labeled to allow immunoblot detection. The secondary antibody is added at a much more dilute level than the primary antibody, from 1:500 to 1:2000 dilution. After incubation, the filter is washed several times in PBS, each wash being about 10 minutes in length. The filter is then placed in a cassette with a piece of Xomat X-ray film (Kodak) at −70° C.

The level of PrP$^{Sc}$ in the affected sample can be determined by comparing the relative levels of signal of each antibody in the affected versus the control mouse. This process can be a physical comparison to determine the relative differences in signal level between the R1 and the 3F4 antibody, or it may be a quantitative comparison. Comparison techniques, both physical and quantitative, will be known to those skilled in the art. Quantitative comparison can be assessed using blot scanning techniques in which the levels are determined using computer programs specially designed to assess comparative levels. One such method is using a modified Excel spreadsheet program. Such programs allow for adjustments between samples based on variables such as background, time of hybridization, etc.

Levels of 3F4 staining should be consistent between the normal control samples of both the R1 and 3F4 antibody blots. The level of difference between R1 staining and 3F4 staining in the affected sample should allow the quantification of PrP$^{Sc}$ in the sample by subtracting the level of PrP$^C$ signal using the 3F4 antibody from the level of PrP$^{Sc}$ and PrP$^C$ signal from R1 antibody.

Such quantification may be adjusted based on antibody sensitivity, concentration, etc.

Example 5

Detection of βA4 in Human and Mouse Brain

A number of mouse models for Alzheimer's disease exhibit many of the hallmark protein changes associated with the human disease. Two examples are: 1) mice with a modified human APP under the control of the PDGF promoter (the "Athena-Lilly mouse"), the production and phenotype of these mice are described in U.S. Pat. No. 5,612,486, and 2) mice with a mutant isoform of human APP under the control of the prion gene promoter (the "Hsiao mouse") see Hsiao et al., *Science* 274:99–102 (1996). These mouse models for Alzheimer's disease display amyloid deposits and are capable of producing all three major APP isoforms, and levels of APP and Aβ40/Aβ42 that progressively increase during the mouse's lifetime.

A 10% (w/v) brain homogenate from normal mice, affected Hsiao mice, and affected Athena mice are prepared in TBS (25 mM Tris). After a low speed centrifugation at 500×g for 15 min, the total protein in the supernatant (S1) is measured using a BCA Protein Assay (Pierce) and the concentration is adjusted to 2.5 mg/ml with PBS.

A Dispase digestion is done at an enzyme to protein ratio of 1:25. The protein is digested with 100 μg/ml Dispase (Worthington) for 60 min at 37° C. in the presence of 0.15% Zwittergent 3–12 (Calbiochem). The digestion is stopped by the addition of 50 mM EDTA. PAGE and transfer of the proteins is performed as in Example 1.

The nylon filter is placed in a heat-sealable plastic bag, and 0.1 ml of blocking solution is added per square cm of filter. The blocking solution contains 5% (w/v) nonfat dry milk (Carnation); 0.01% antifoam A; and 0.02% sodium azide in PBS. After 1 hour shaking at room temperature, a monoclonal antibody recognizing the β-amyloid protein, such as RDI-BAMYLOID (Research Daignostics) is added in a 1:200 dilution, and the filter incubated for 2–4 hours at 4° C. with gentle agitation on a platform shaker. Following incubation, the blocking solution and antibody are removed, and the filter washed three times.

The filter is incubated with an anti-mouse Ig secondary antibody in blocking solution for 1–2 hours at room temperature. The secondary antibody is radiolabeled with to allow immunoblot detection. For the radiolabeled I$^{125}$ probe, approximately 10$^4$ cm of the reagent is added per square centimeter of filter. After incubation, the filter is washed several times in PBS, each wash being about 10 minutes in length. The filter is placed in a cassette with a piece of Xomat X-ray film (Kodak) at −70° C.

The resulting blot will have a band corresponding to βA4 in the sample of the treated Athena Lilly or Hsiao mouse brain, both before and after digestion with Dispase. The sample of the normal mouse brain protein may show a low level band due to background with the APP protein. The lane with the normal brain sample subjected to hydrolysis with Dispase should not have a detectable band, since the Dispase will have hydrolysed the normal protein in the sample.

This protocol may also be used with human brain or biopsy material, to identify and diagnose individuals suspected of having Alzheimer's disease.

Example 6

Detection of TTR in Biopsy Material

A biopsy sample from the liver is taken from an individual thought to be suffering from familial amyloid polyneuropathy (FAP). Homogenates (10% (w/v)) of the liver sample and a normal liver control sample are prepared in TBS (25 mM Tris). After a low speed centrifugation at 500×g for 15 min, the total protein in the supernatant (S1) is measured using a BCA Protein Assay (Pierce) and the concentration is adjusted to 3.5 mg/ml with PBS.

A Neprilysin digestion is done at an enzyme to protein ratio of 1:35. The protein is digested with 100 μg/ml Dispase for 60 min at 37° C. in the presence of 0.2% Sarkosyl. The digestion is stopped by the addition of 50 mM EDTA. An aliquot of the proteins obtained in S1 both before and after the neprilysin digestion is electrophoresed at 4° C. on an 8% polyacrylamide slab gel as described in Example 2, i.e. under nondenaturing conditions. The gel is run and proteins are transferred to nylon as in Example 1.

The nylon filter is placed in a heat-sealable plastic bag, and 0.1 ml of blocking solution is added per square cm of filter. The blocking solution contains 5% (w/v) nonfat dry milk (Carnation) and 0.02% sodium azide in PBS. After 1 hour shaking at room temperature, a monoclonal antibody recognizing the amyloid conformation of TTR is added in a 1:100 to 1:500 dilution, and the filter incubated for 2–4 hours at 4° C. with gentle agitation on a platform shaker. Following incubation, the blocking solution and antibody are removed, and the filter washed three times.

The secondary antibody is enzyme-conjugated with horseradish peroxidase to allow immunoblot detection. The secondary antibody is added at a much more dilute level than the primary antibody, from 1:500 to 1:2000 dilution. After incubation, the filter is washed several times in PBS, each wash being about 10 minutes in length. The filter is then placed in a cassette with a piece of Xomat X-ray film (Kodak) at −70° C.

The resulting blot will have a band corresponding to the amyloid conformation of TTR in an affected biopsy sample, but not in a biopsy sample in which the amyloids are not present. Moreover, the concentration of the TTR amyloid conformation may be a prognostic indicator as to the severity of the disease, and biopsies using multiple samples may also be used to determine disease progression.

The instant invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

What is claimed is:

1. A method of isolating a PrP$^{Sc}$ protein, comprising:
   treating a sample suspected of containing PrP$^C$ protein and PrP$^{Sc}$ protein with a compound which hydrolyzes the PrP$^C$ protein but not PrP$^{Sc}$ protein to provide a treated sample; and
   separating the PrP$^{Sc}$ protein away from the treated sample.

2. The method of claim 1, wherein the compound which hydrolyzes PrP$^C$ but not PrP$^{Sc}$ is dispase.

3. The method of claim 1, wherein the separating is carried out by centrifuging the treated sample.

4. An assay method, comprising:
treating a sample suspected of containing $PrP^C$ protein and $PrP^{Sc}$ protein with a compound which hydrolyzes the $PrP^C$ protein but not $PrP^{Sc}$ protein to provide a treated sample; and
separating the $PrP^{Sc}$ protein away from the treated sample; concentrating the treated $PrP^{Sc}$;
contacting the concentrate of treated $PrP^{Sc}$ with a binding partner;
determining the presence of $PrP^{Sc}$ in the sample based on a level of binding to the binding partner.

5. The assay of claim 4, wherein the separating is carried out by centrifuging the treated sample.

6. The assay method of claim 4, wherein the compound which hydrolyzes $PrP^C$ but not $PrP^{Sc}$ is dispase.

7. The assay method of claim 4, wherein the compound which hydrolyzes $PrP^C$ but not $PrP^{Sc}$ is a metalloendopeptidase.

8. The assay method of claim 4, wherein the binding partner is an antibody.

9. The assay method of claim 4, wherein the sample is obtained from a mammal.

10. The assay method of claim 4, wherein the sample comprises brain tissue from a mammal selected from the group consisting of human, sheep and cow.

11. The method of claim 4, wherein the binding partner is bound to a detectable label.

12. The method of claim 11, wherein the detectable label is a fluorescent label and further wherein determining the presence of $PrP^{Sc}$ in the treated sample is carried out using time-resolved dissociation enhanced fluorescence.

13. The method of claim 11, wherein the detectable label is a fluorescent label and further wherein determining the presence of $PrP^{Sc}$ in the treated sample is carried out using a dual wavelength, laser driven fluorometer.

* * * * *